US010835192B2

(12) United States Patent
Joung et al.

(10) Patent No.: US 10,835,192 B2
(45) Date of Patent: Nov. 17, 2020

(54) X-RAY IMAGING METHOD USING VARIABLE IMAGING PLANE PROJECTION AND X-RAY IMAGING DEVICE APPLYING THE SAME

(71) Applicant: NuCare, Inc., Incheon (KR)

(72) Inventors: Jinhun Joung, Incheon (KR); Yong-Kwon Kim, Chuncheongnam-do (KR); Manh Hung Nguyen, Incheon (KR)

(73) Assignee: NuCare, Inc., Incheon (KR)

( * ) Notice: Subject to any disclaimer, the term of this patent is extended or adjusted under 35 U.S.C. 154(b) by 220 days.

(21) Appl. No.: 16/154,234

(22) Filed: Oct. 8, 2018

(65) Prior Publication Data

US 2020/0069265 A1    Mar. 5, 2020

(30) Foreign Application Priority Data

Aug. 31, 2018 (KR) .................. 10-2018-0103852

(51) Int. Cl.
| | | |
|---|---|---|
| G06K 9/00 | (2006.01) | |
| A61B 6/00 | (2006.01) | |
| A61B 6/08 | (2006.01) | |

(52) U.S. Cl.
CPC .......... *A61B 6/4085* (2013.01); *A61B 6/4071* (2013.01); *A61B 6/4078* (2013.01); *A61B 6/08* (2013.01); *A61B 6/4021* (2013.01); *A61B 6/5223* (2013.01)

(58) Field of Classification Search
None
See application file for complete search history.

(56) References Cited

U.S. PATENT DOCUMENTS

| | | | | |
|---|---|---|---|---|
| 8,588,364 B2* | 11/2013 | Suzuki | ................... | A61B 6/469 |
| | | | | 378/40 |
| 2013/0114799 A1* | 5/2013 | Yamakawa | .............. | A61B 6/14 |
| | | | | 378/207 |
| 2017/0322271 A1* | 11/2017 | Gulaka | ................ | A61B 5/0555 |
| 2018/0310898 A1* | 11/2018 | Ahn | ....................... | A61B 6/469 |
| 2020/0029919 A1* | 1/2020 | Senegas | ............... | A61B 6/4452 |

* cited by examiner

*Primary Examiner* — Atiba O Fitzpatrick
(74) *Attorney, Agent, or Firm* — Levenfeld Pearlstein, LLC

(57) ABSTRACT

The present disclosure relates to an x-ray imaging method using a variable imaging plane projection and to an x-ray imaging device applying the same. By applying a variable imaging plane projection using at least two sets of scan data for different heights obtained while varying the height of the x-ray generator from an imaging object, it is possible to solve problems caused due to a magnification effect generated in the x-ray imaging field based on a fan-beam-type or cone-beam-type x-ray generator, thereby providing more accurate x-ray image information.

22 Claims, 16 Drawing Sheets

X-RAY IMAGING METHOD USING VARIABLE IMAGING PLANE PROJECTION AND X-RAY IMAGING DEVICE APPLYING THE SAME

BACKGROUND OF THE INVENTION

1. Field of the Invention

The present disclosure relates to an x-ray imaging method and an x-ray imaging device applying the same, and more particularly to an x-ray imaging method based on a fan-beam-type or cone-beam-type x-ray generator that is capable of eliminating a magnification effect occurring in the field of x-ray imaging, and an x-ray imaging device applying the same.

2. Description of the Prior Art

As is well known, imaging techniques using x-rays have a very wide and long history in medical and industrial applications, and have been very useful.

An x-ray imaging device basically includes an x-ray generator configured to radiate x-rays toward an imaging object and an x-ray detector disposed such that an imaging object is interposed between the x-ray generator and the x-ray detector and configured to detect x-rays transmitted through the imaging object.

The x-ray generator is classified into a pencil-beam type, a fan-beam type, or a cone-beam type depending on the shape of the Field of View (FOV) of the x-ray, and the x-ray detector used in correspondence with the x-ray generator is classified into a single type, a one-dimensional-array (1D array) type, or a two-dimensional-array (2D array) type.

Of course, in a field requiring a tomographic image of a three-dimensional volume, the x-ray generator and the x-ray detector are configured to collect data necessary to create a three-dimensional image while rotating.

However, as shown in FIG. 1, in the case of the x-ray imaging device 100 based on the fan-beam-type or cone-beam-type x-ray generator 10, an x-ray image 211 or 221 magnified to be larger than the size of an imaging target object 210 or 220 within an original imaging object 200 is projected onto the x-ray detector 20 due to a magnification effect.

Furthermore, as the imaging target object 210 or 220 in the imaging object 200 moves away from the x-ray detector 20, the magnification effect described above increases.

Since the magnification effect varies depending on the distance between the imaging target object 210 or 220 and the x-ray detector 20 as described above, there is a problem in that the position and size of an actual imaging target object 210 or 220 cannot be accurately provided.

SUMMARY OF THE INVENTION

An aspect of the present disclosure is to provide an x-ray imaging method capable of solving problems caused due to a magnification effect by obtaining scan data of different heights by varying the height of an x-ray generator and applying a variable imaging plane projection using the acquired scan data so as to infer the actual position and size of an imaging target object in an imaging object, and an x-ray imaging device applying the x-ray imaging method.

In order to achieve the aspect described above, the present disclosure provides an x-ray imaging method using an x-ray imaging device having an x-ray generator and an x-ray detector which are disposed such that an imaging object is interposed therebetween. The x-ray imaging method includes: obtaining at least two sets of scan data for different heights by varying a height of the x-ray generator from the x-ray detector; and applying a variable imaging plane projection using the at least two sets of obtained scan data to image an imaging target object in the imaging object at an actual position and size.

By applying the variable imaging plane projection using the following equation eq1 obtained through preorder scan data and the following equation eq2 obtained through postorder scan data, it is possible to calculate the correct size d of an imaging target object according to a height x from the imaging plane to the imaging target object.

$$\tan\theta_1 = \frac{D_1}{H_1} = \frac{d}{H_1 - x} \quad \text{eq1}$$

$$\tan\theta_2 = \frac{D_2}{H_2} = \frac{d}{H_2 - x} \quad \text{eq2}$$

Here, $H_1$ and $H_2$ are heights of the x-ray generator during a preorder scan $S_1$ and a postorder scan $S_2$, $D_1$ and $D_2$ are projected sizes of the imaging target object projected on the x-ray detector, $\theta_1$ and $\theta_2$ are respective projection angles at which an x-ray is projected onto the imaging target object during the preorder scan $S_1$ and the postorder scan $S_2$, x is a height from the imaging plane to the imaging target object, and d is the actual size of the imaging target object.

Here, the arithmetic controller sets variable heights of the imaging target object consecutively determined along a scan direction to x-ray projection points at respective positions at arbitrary moments by applying the variable imaging plane projection, and causes the imaging target object to be projected in a calculated actual size by varying the imaging plane with respect to each of the heights at the arbitrary moments.

In addition, the x-ray generator may use a fan beam, and the x-ray detector may be configured in a one-dimensional-array (1D array) type. In this case, the resolution can be doubled by causing, during the postorder scan, the scan to be performed after the x-ray generator is selectively shifted horizontally with a difference of a half pixel of the x-ray detector in comparison with the preorder scan, or by causing, during the postorder scan, the scan to be performed after the x-ray detector is shifted horizontally with a difference of a half pixel in comparison with the preorder scan, and combining the two sets of data.

In addition, the x-ray generator may use a cone beam, and the x-ray detector may be configured in a two-dimensional-array (2D array) type. In this case, the resolution can be doubled by causing, during the postorder scan, the scan to be performed after the x-ray generator is selectively shifted in each of vertical and horizontal directions with a difference of a half pixel of the x-ray detector in comparison with the preorder scan, or by causing, during the postorder scan, the scan to be performed after the x-ray detector is shifted in each of vertical and horizontal directions with a difference of a half pixel of the x-ray detector in comparison with the preorder scan, and combining the two sets of data.

In addition, the x-ray detector may be configured in a flat plate shape or an arc shape. In particular, when the x-ray detector is configured in the arc shape, it is preferable that the x-ray focal point of the x-ray generator be positioned at the arc center of the x-ray detector such that the respective pixels of the x-ray detector are located at the same distance from the x-ray generator.

In addition, when the scan is performed twice while varying the height of the x-ray generator, a dual-energy imaging method may be applied while varying the energy of the x-ray during each scan.

In addition, an x-ray imaging device applying a variable imaging plane projection according to the present disclosure may include: an x-ray generator configured to generate an x-ray; an x-ray detector disposed such that an imaging object is interposed between the x-ray generator and the x-ray detector, and configured to detect the x-ray transmitted through the imaging object; a first position-varying unit configured to vary the height of the x-ray generator from the imaging object; and an arithmetic controller configured to obtain at least two sets of scan data for different heights while varying the height of the x-ray generator from the x-ray detector, and to image the imaging object at an actual position and size by applying a variable imaging plane projection using the at least two sets of obtained scan data.

Here, the arithmetic controller is configured to calculate the correct size d of an imaging target object according to a height x from the imaging plane to the imaging target object by applying the variable imaging plane projection using the following equation eq1 obtained through preorder scan data, and the following equation eq2 obtained through postorder scan data.

$$\tan\theta_1 = \frac{D_1}{H_1} = \frac{d}{H_1 - x} \qquad \text{eq1}$$

$$\tan\theta_2 = \frac{D_2}{H_2} = \frac{d}{H_2 - x} \qquad \text{eq2}$$

Here, $H_1$ and $H_2$ are heights of the x-ray generator 10 during a preorder scan $S_1$ and a postorder scan $S_2$, $D_1$ and $D_2$ are projected sizes of the imaging object 210 projected on the x-ray detector 20, $\theta_1$ and $\theta_2$ are respective projection angles at which an x-ray is projected on the imaging target object during the preorder scan $S_1$ and the postorder scan $S_2$, x is a height from the imaging plane to the imaging target object, and d is the actual size of the imaging target object.

In addition, the arithmetic controller is configured to set variable heights of the imaging target object consecutively determined along a scan direction to x-ray projection points at respective positions at arbitrary moments by applying the variable imaging plane projection, and to cause the imaging target object to be projected at a calculated actual size by varying the imaging plane with respect to each of the heights at the arbitrary moments.

Here, the x-ray generator may be configured in a fan-beam type, and the x-ray detector may be configured in a one-dimensional-array (1D array) type.

At this time, during the postorder scan, through the first position-varying unit, the scan may be performed after the x-ray generator is shifted horizontally with a difference of a half pixel of the x-ray detector in comparison with the preorder scan.

In addition, the x-ray imaging device may further include a second position-varying unit configured to vary the position of the x-ray detector. In this case, during the postorder scan, through the second position-varying unit, the scan may be performed after the x-ray detector is shifted horizontally with a difference of a half pixel of the x-ray detector, in comparison with the preorder scan.

In addition, the x-ray generator may be configured in a cone-beam type, and the x-ray detector may be configured in a two-dimensional-array (2D array) type.

At this time, during the postorder scan, through the first position-varying unit, the scan may be performed after the x-ray generator is shifted in each of the vertical and horizontal directions with a difference of a half pixel of the x-ray detector in comparison with the preorder scan.

In addition, the x-ray imaging device may further include a second position-varying unit configured to vary the position of the x-ray detector. In this case, during the postorder scan, through the second position-varying unit, the scan may be performed after the x-ray detector is shifted in each of the vertical and horizontal directions with a difference of a half pixel of the x-ray detector in comparison with the preorder scan.

In addition, the x-ray detector may be configured in a flat plate shape or an arc shape. Here, when the x-ray detector is configured in an arc shape, it is preferable that the x-ray focal point of the x-ray generator be located at the center of the arc of the x-ray detector.

Further, it is preferable that the x-ray generator be configured to vary x-ray energy during each scan when performing the scan twice while varying the height.

According to an x-ray imaging method applying a variable imaging plane projection according to the present disclosure and an x-ray imaging device applying the x-ray imaging method, by applying a variable imaging plane projection using at least two sets of scan data for different heights obtained while varying the height of the x-ray generator from an imaging object, it is possible to solve problems caused due to a magnification effect generated in the x-ray imaging field based on a fan-beam-type or cone-beam-type x-ray generator, thereby providing more accurate x-ray image information.

In addition, since it is necessary to scan the entire imaging object at least twice while changing the height of the x-ray generator, unlike the conventional x-ray imaging, when a fan beam is used, imaging is performed after shifting the 1D array x-ray detector in the horizontal direction by a half pixel between the preorder scan and the postorder scan, or when a cone beam is used, the scan is performed after shifting the 2D array x-ray detector in the vertical and horizontal directions by a half pixel and the two sets of data are combined, so that the resolution can be doubled.

In addition, by generating two different kinds of x-ray energy so as to obtain an image, and by applying a "dual energy imaging" method, which is a kind of x-ray imaging method that obtains images and distinguishes hard tissue and soft tissue from each other using the difference, so as to obtain data by varying each x-ray energy when scanning is performed twice while varying the height of the x-ray generator, it is possible to extensively apply the present disclosure to a baggage-screening stage at a port facility and to the field of osteoporosis testing.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
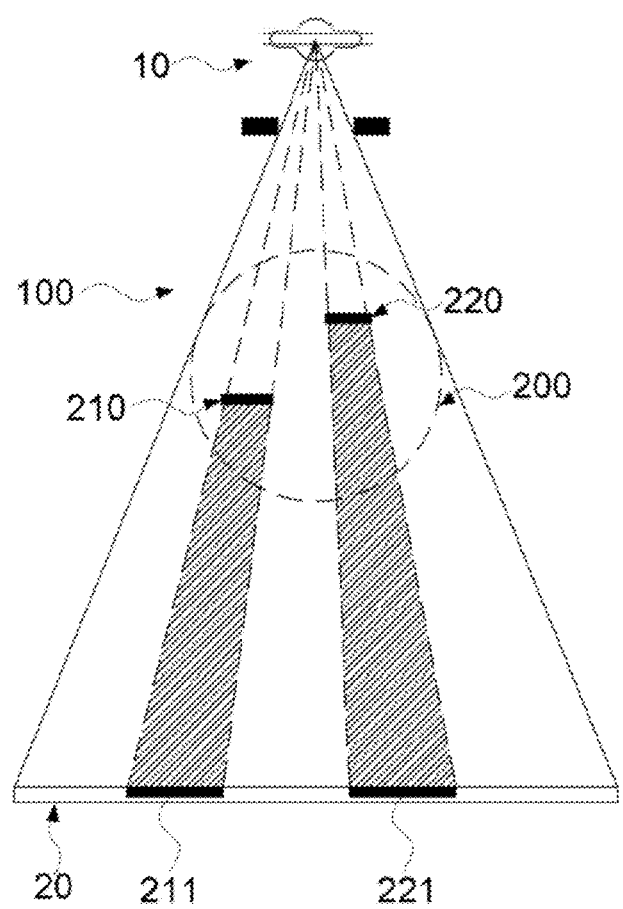
FIG. 1 is a schematic view illustrating a magnification effect generated when a cone beam or a fan beam is used.

Hereinafter, embodiments of the present disclosure will be described in detail with reference to the accompanying drawings such that those skilled in the art can easily carry out the present disclosure. However, the present disclosure may be implemented in many different forms and is not limited to the embodiments described herein. In order to clearly describe the present disclosure, parts not related to the description are omitted, and the same or similar components are denoted by the same reference numerals throughout the specification.

Figure 2:
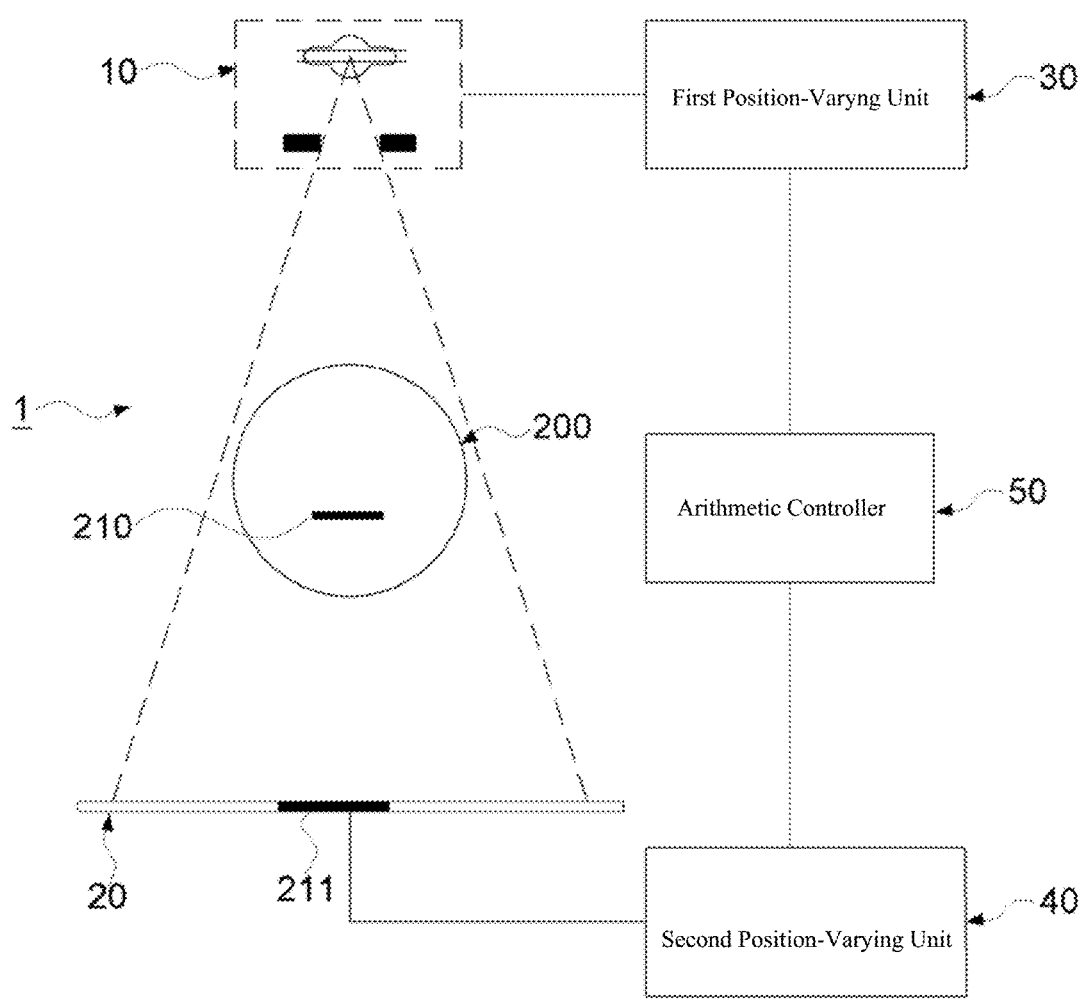
FIG. 2 is a schematic view illustrating an x-ray imaging device according to an embodiment of the present disclosure.

FIG. 2 is a schematic view illustrating an x-ray imaging device according to the present disclosure.

Referring to FIG. 2, an x-ray imaging device 1, which applies an x-ray imaging method using variable imaging plane projection of the present disclosure, includes an x-ray generator 10, an x-ray detector 20, a first position-varying unit 30, a second position-varying unit 40, and an arithmetic controller 50.

Here, the x-ray imaging device 1 is basically configured such that the x-ray detector 20 is disposed with an imaging object 200 being interposed between the x-ray generator 10 and the x-ray detector 20 such that the x-ray detector 20 detects an x-ray generated in the x-ray generator 10 and transmitted through the imaging object 200 so as to image an imaging target object 210 in the imaging object 200.

Here, as the x-ray generator 10, a fan-beam-type or cone-beam-type x-ray generator, in which a magnification effect is generated, may be mainly used, and the x-ray detector 20 may be configured in a 1D-array or 2D-array type constituted with a plurality of x-ray sensors corresponding to the x-ray generator 10.

The first position-varying unit 30 is configured to vary the height up to the x-ray generator 10 configured to generate an x-ray from the x-ray detector 20.

Figure 3:
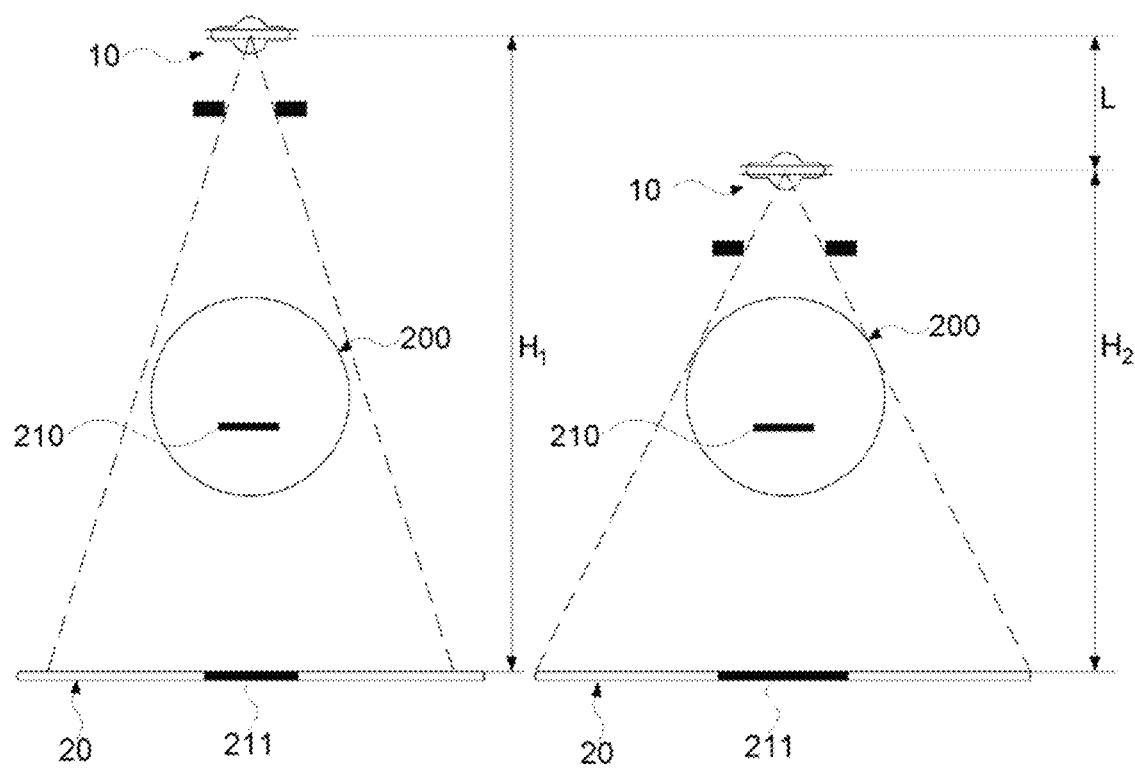
FIG. 3 is a schematic view illustrating a state where the height of an x-ray generator is varied through the first position-varying unit.

FIG. 3 is a schematic view illustrating the state where the height of an x-ray generator is varied through the first position-varying unit.

Referring to FIG. 3, the x-ray generator 10 is shifted vertically toward the x-ray detector 20 through the first position-varying unit 30 so as to vary the height up to the x-ray generator 10 from the x-ray detector 20 from $H_1$ to $H_2$.

Here, it is obvious that the range L for the variable height of the x-ray generator 10 can be variously modified and applied according to the type and form of the applied x-ray imaging device.

Meanwhile, the first position-varying unit 30 may be configured to be capable of performing both an operation of shifting the x-ray generator 10 in order to scan the imaging object 200 and an operation of shifting the x-ray generator 10 in the horizontal direction or in the vertical and horizontal directions by a half pixel during a postorder scan $S_2$, in comparison with a preorder scan $S_1$, in order to increase the resolution as described below.

In addition, as another method of increasing the resolution, the second position-varying unit 40 may be configured to shift the x-ray detector 20 in the horizontal direction by a half pixel during the postorder scan $S_2$, in comparison with the preorder scan $S_1$, as well as to vary the position of the x-ray detector 20 in both the vertical and horizontal directions when necessary.

Further, the arithmetic controller 50 varies the height of the x-ray generator 10 from the imaging object 200 through the first position-varying unit 30 to obtain two or more sets of scan data for different heights and then imaging the imaging target object 210 at the actual position and size by applying variable imaging plane projection using the at least two sets of obtained scan data.

Figure 4:
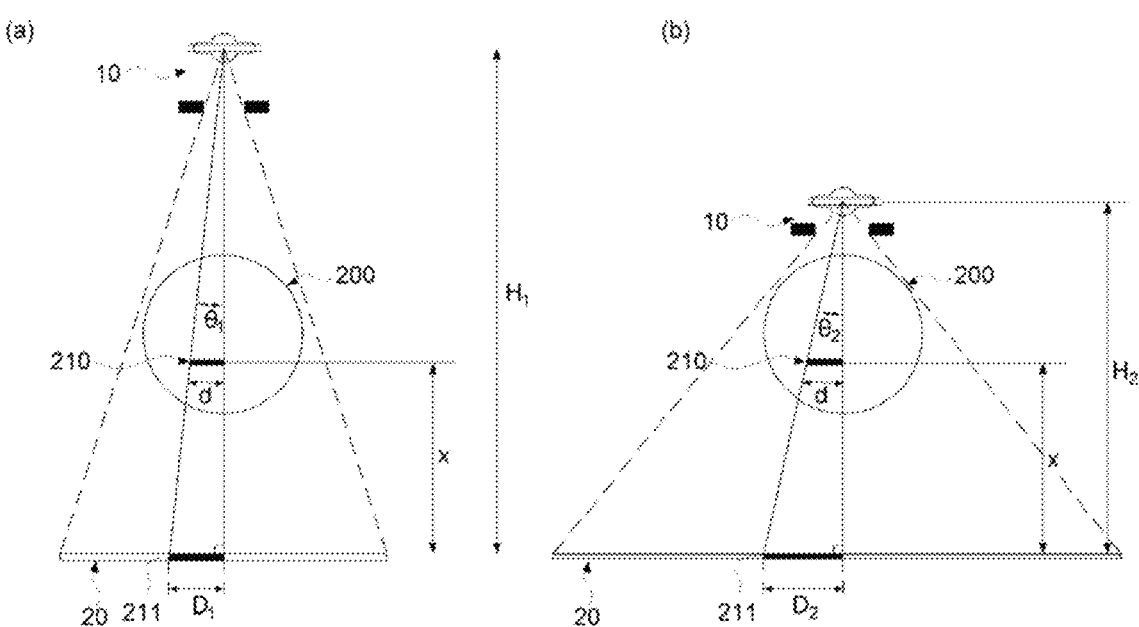
FIG. 4 is a schematic view illustrating the process of obtaining x-ray images while varying the height of the x-ray detector as illustrated in FIG. 3.

FIG. 4 is a schematic view illustrating a process of obtaining x-ray images of the same imaging object while varying the height of the x-ray detector as illustrated in FIG. 3.

Referring to FIG. 4, in order to minimize the magnification effect generated in the fan-beam-type or cone-beam-type x-ray generator 10, when the relative position of the imaging target object 210 in the imaging object 200, i.e. the relative height x from the x-ray detector 20 to the imaging target object 210 is known, the actual size d can be determined. This may be calculated from respective measurements $D_1$ and $D_2$ collected over two scans and projected onto the x-ray detector 20.

In the present embodiment, it is exemplified that the x-ray generator 10 is a fan-beam-type x-ray generator and that an x-ray detector 20 in which x-ray sensors are arranged in the form of a 1D array to correspond to the fan-beam-type x-ray generator 10 is used as the x-ray detector 20.

However, the present disclosure is not necessarily limited to this. As described above, it is obvious that a cone-beam-type x-ray generator may be used as the x-ray generator 10 and that an x-ray detector 20 in which x-ray sensors are arranged in the form of a 2D array to correspond to the x-ray generator 10 may be used as the x-ray detector 20.

Accordingly, the heights of the x-ray generator 10 during the first scan $S_1$ and the second scan $S_2$, which are at least required for imaging the imaging target object 210 in the imaging object 200 at the actual position and size by applying variable imaging plane projection using the two sets of scan data, are defined as $H_1$ and $H_2$, respectively, and the magnitudes of the imaging target object 210 projected on the x-ray detector 20 during the first scan $S_1$ and the second scan $S_2$ are defined as $D_1$ and $D_2$, respectively.

When the projection angles at which x-rays are projected onto the imaging target object 210 are defined as $\theta_1$ and $\theta_2$, the following two equations can be produced, and based on the trigonometric function method, two variables x (the height from the imaging plane of the x-ray detector to the imaging target object) and d (the actual width of the imaging target object) can be obtained through these equations.

Equation 1
$$\tan\theta_1 = \frac{D_1}{H_1} = \frac{d}{H_1 - x} \qquad \text{eq1}$$

Equation 2
$$\tan\theta_2 = \frac{D_2}{H_2} = \frac{d}{H_2 - x} \qquad \text{eq2}$$

That is, when the height x from the imaging plane to the imaging target object 210 is obtained first, the correct size d of the corresponding imaging target object 210 can be obtained.

Then, by expanding a series of work processes described above in two dimensions, a two-dimensional image can be obtained.

Figure 5:
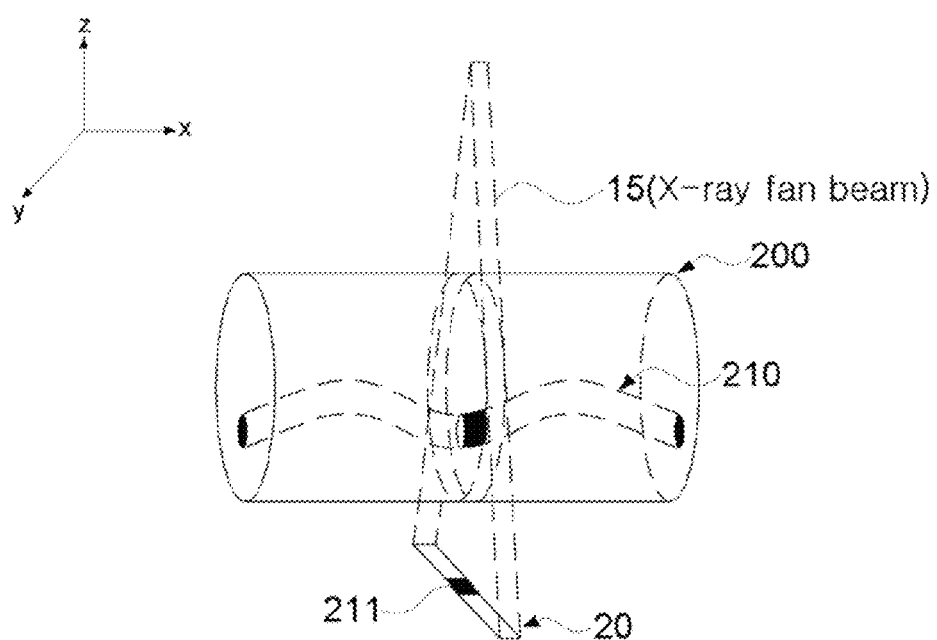
FIG. 5 is a schematic view for explaining an imaging plane projected at an arbitrary moment.

FIG. 5 is a schematic view for explaining an imaging plane projected at any moment.

Referring to FIG. 5, when an imaging target object 210 is irregularly and continuously arranged in the x-axis direction with different heights from the x-ray detector 10 in a cylindrical imaging object 200 having a constant diameter, a cross section projected onto the x-ray detector 20 by emitting a fan beam 15 of the x-ray generator 10 with a thickness t to the imaging target object 210 at an arbitrary moment during the scan of the imaging target object 210 may be defined as a one-dimensional projection (1D projection).

At this time, when 1D projections collected at each moment are arranged on the x-y plane by moving the fan-beam-type x-ray generator 15 and the x-ray detector 20 together in the x-axis direction, a two-dimensional projection (2D projection) of the imaging target object 210, that is, a two-dimensional x-ray image, can be obtained.

Figure 6:
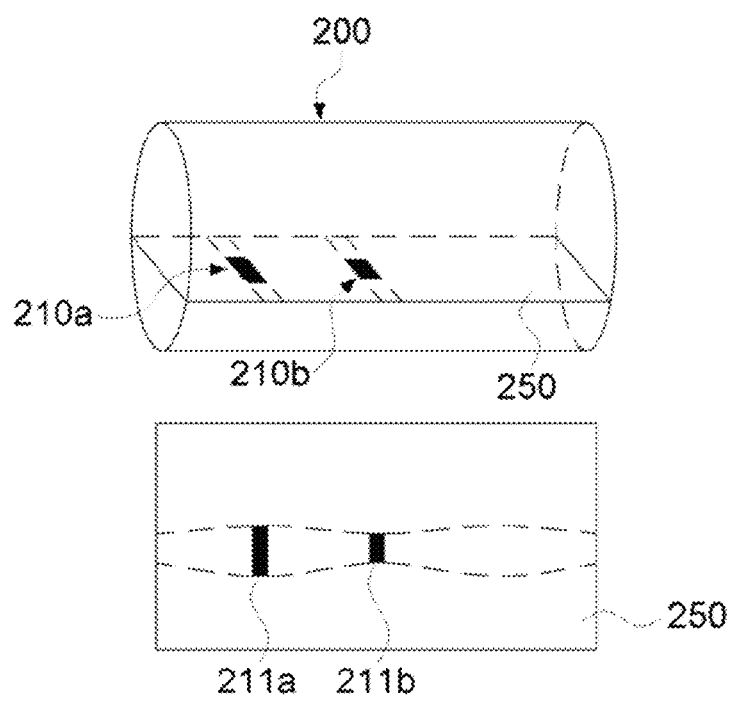
FIG. 6 is a two-dimensional x-ray imaging plane obtained by applying a conventional fixed imaging plane projection to the imaging object of FIG. 5.
Figure 7:
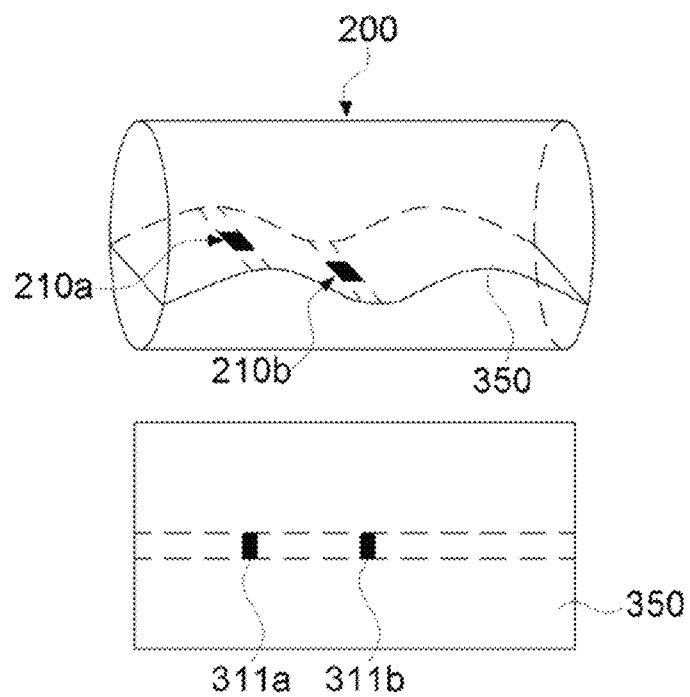
FIG. 7 is a two-dimensional x-ray imaging plane obtained by applying a variable imaging plane projection of the present disclosure to the imaging object of FIG. 5.

FIG. 6 is a two-dimensional x-ray imaging plane obtained by applying a conventional fixed imaging plane projection to the imaging object of FIG. 5, and FIG. 7 is a two-dimensional x-ray imaging plane obtained by applying a variable imaging plane projection of the present disclosure to the imaging object of FIG. 5.

As illustrated in FIG. 6, when a conventional fixed imaging plane projection is applied to the imaging target object 210 of FIG. 5, in the x-ray images 211a and 211b projected onto fixed imaging planes 250 preset at an arbitrary height with respect to respective positions 210a and 210b at different heights in the imaging target object 210, an error (distortion) occurs due to a magnification effect caused by the height difference therebetween.

However, as illustrated in FIG. 7, when an x-ray imaging method using the variable imaging plane projection proposed in the present disclosure is applied to the imaging object of FIG. 5, it is possible to eliminate an error (distortion) caused due to a magnification effect in x-ray images 311a and 311b projected from two positions 210a and 210b at different heights of the imaging target object 210 by applying the variable imaging plane projection using at least two sets of scan data for different heights while varying the height of the x-ray generator 10 so as to image the imaging target object 210 in the imaging object 200 at the actual position and size.

As described above, in order to solve the error caused due to the magnification effect described above by applying the variable imaging plane projection, it is necessary to obtain at least two sets of scan data while varying the height of the x-ray generator 10 first.

That is, in order to calculate the relative height x from the x-ray detector 20 to the imaging target object 210, at least two sets of scan data are essential.

Then, the height variation of the imaging target object 210 with respect to the respective positions 210a and 210b is continuously detected from the imaging plane through the at least two sets of scan data, and based on the height variation, variable imaging plane projection is applied such that the actual sizes 311a and 311b are calculated and projected through correction with respect to the imaging plane.

That is, the variable imaging plane projection sets the variable heights of the imaging target object 210 consecutively determined along the scan direction to x-ray projection points at respective positions at arbitrary moments, and causes the imaging target object 210 to be projected in the calculated actual size by varying the imaging plane with respect to each of the heights at the arbitrary moments.

FIG. 7 represents a variable imaging plane 350 varied by consecutively determining the variable height x of an imaging target object 210 calculated in each imaging plane in the total imaging section of the imaging target object 210 and reflecting the determined variable height. Meanwhile, when the fan-beam-type x-ray generator 10 is used, as in the present embodiment, the resolution can be doubled by causing, during the postorder scan, the scan to be performed after the x-ray generator is selectively shifted horizontally through the primary position-varying unit with a difference of a half pixel of the x-ray detector, in comparison with the preorder scan, or by causing, during the postorder scan, the scan to be performed after the x-ray detector is shifted horizontally through the secondary position-varying unit with a difference of a half pixel in comparison with the preorder scan, and combining the two sets of data.

Figure 8:
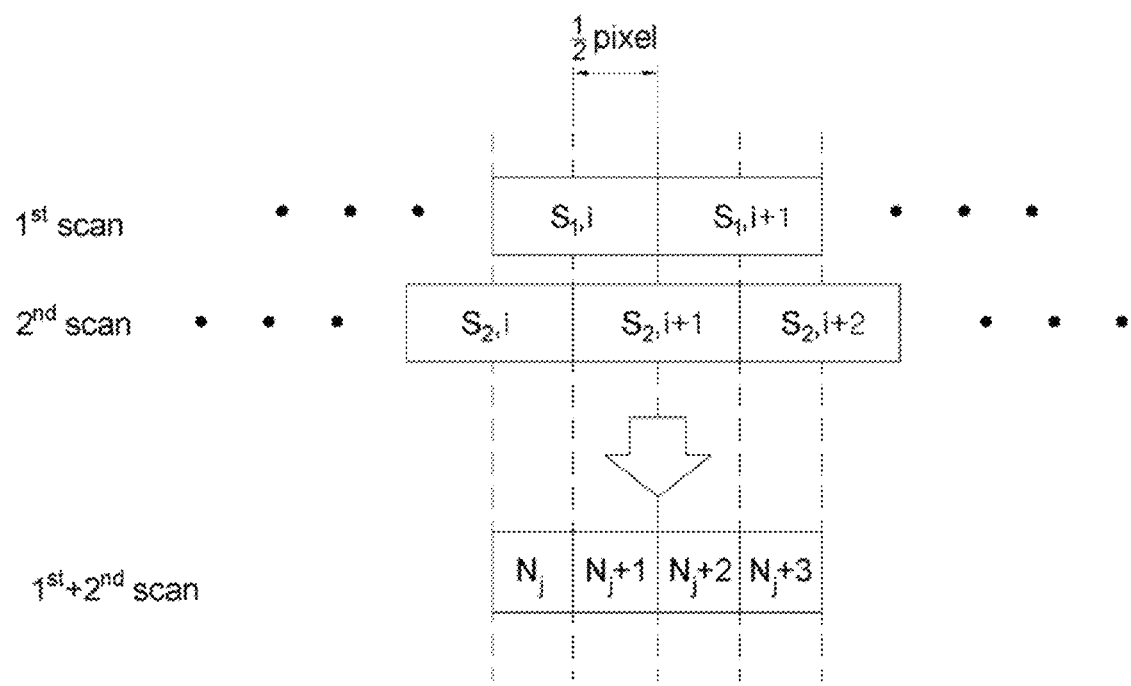
FIG. 8 is a schematic view illustrating a process of doubling a resolution by shifting a 1D array detector in the horizontal direction by a half pixel in an x-ray image in the form of a fan beam.

FIG. 8 is a schematic view illustrating a process of doubling a resolution by shifting a 1D array detector in the horizontal direction by a half pixel in an x-ray image in the form of a fan beam.

Referring to FIG. 8, when arbitrary pixels during a first scan are defined as $S_{1,i}$ and $S_{1,i+1}$ and corresponding pixels during a second scan, which is shifted by a half pixel as described above, are defined as $S_{2,i}$, $S_{2,i+1}$, and $S_{2,i+2}$, newly defined pixels may be defined as $N_j$, $N_{j+1}$, $N_{j+2}$, and $N_{j+3}$, the size of which is half of the original pixel size, thereby doubling the resolution.

The values of the newly defined pixels are defined as represented in Equation 3 below.

$$N_j = \frac{S_{2,i} + S_{1,i}}{2}$$

$$N_{j+1} = \frac{S_{1,i} + S_{2,i+1}}{2}$$

$$N_{j+2} = \frac{S_{2,i+1} + S_{1,i+1}}{2}$$

$$N_{j+3} = \frac{S_{1,i+1} + S_{2,i+2}}{2}$$

Equation 3

Figure 9:
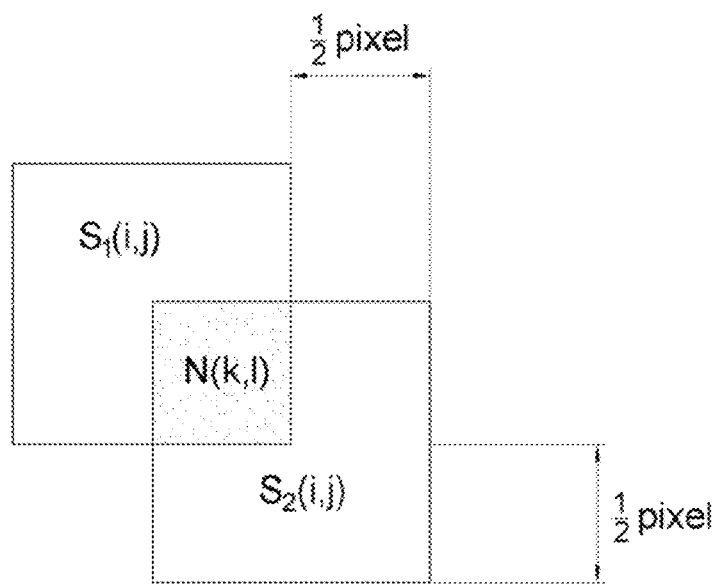
FIG. 9 is a schematic view illustrating a process of doubling a resolution by shifting a 2D array detector in each of the vertical and horizontal directions by a half pixel in an x-ray image in the form of a cone beam.

FIG. 9 is a schematic view illustrating a process of doubling a resolution by shifting a 2D array detector in each of the vertical and horizontal directions by a half pixel in an x-ray image in the form of a cone beam.

Referring to FIG. 9, when the cone-beam-type x-ray generator 10 is used as a modification to the present embodiment, by applying the above-described method extensively in the following manner, the resolution can be doubled by selectively causing, during the postorder scan, the scan to be performed after the x-ray generator is shifted in each of the vertical and horizontal directions with a difference of a half pixel through the primary position-varying unit in comparison with the preorder scan, or by causing, during the postorder scan, the scan to be performed after the x-ray detector is shifted in each of the vertical and horizontal directions with a difference of a half pixel through the secondary position-varying unit in comparison with the preorder scan.

That is, when the cone-beam-type x-ray detector 10 is used, the area $N_{(k,l)}$ produced by shifting the preorder and postorder scans by a half pixel in each of the vertical and horizontal directions can be obtained by Equation 5 as follows.

$$N_{(k,l)} = \frac{S_{1(i,j)} + S_{2(i,j)}}{4}$$

Equation 5

Figure 10:
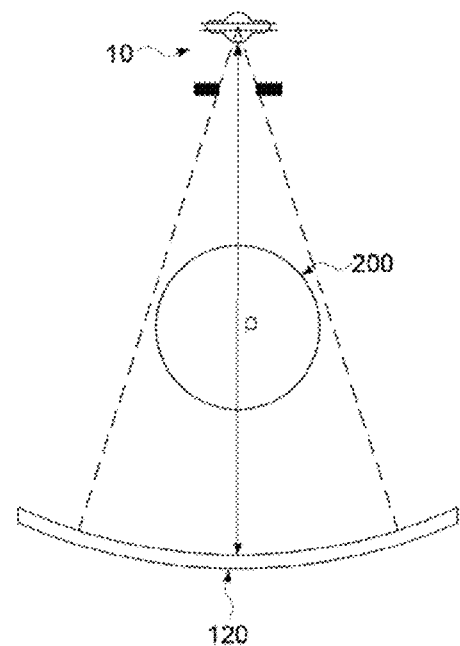
FIG. 10 is a schematic view of an x-ray imaging device to which an arc-shaped x-ray detector is applied.

FIG. 10 is a schematic view of an x-ray imaging device to which an arc-shaped x-ray detector is applied.

Referring to FIG. 10, the x-ray detector 120 may have an arc shape having a predetermined curvature, in addition to the flat plate shape described above.

When the x-ray detector 120 has an arc shape, it is preferable that the x-ray focal point of the x-ray generator 10 be positioned at the arc center of the x-ray detector 120 such that the respective pixels of the x-ray detector 120 are located at the same distance from the x-ray generator 10.

Test Example

An x-ray imaging method that images an imaging target object in an imaging object at an actual position and size by applying a variable imaging plane projection of the present disclosure using at least two sets of scan data for different heights was verified through a Monte-Carlo simulation test, which will be described below with reference to FIGS. 10 to 16.

In the test example, in order to verify the x-ray imaging method using the variable imaging plane projection, two sets of scan data were obtained under the following conditions using a GATE [1] Monte-Carlo simulation tool.

In this case, as the x-ray generator 10 of the x-ray imaging device that was used, a fan-beam-type x-ray generator was applied, and the corresponding x-ray detector 20 was a 1×16 array type of a 1D type in which each sensor was configured to be 3×3 mm in size.

Figure 11:
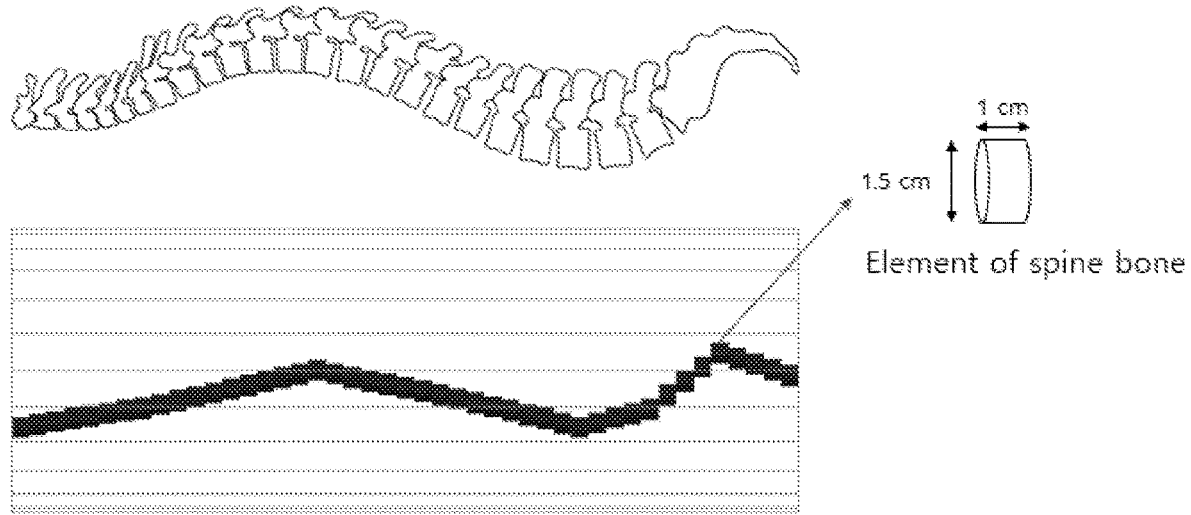
FIG. 11 illustrates a human vertebral bone, which was used as an imaging target object when performing simulation (Monte Carlo simulation) to verify the effect of the present disclosure and a diagram simulating the structure of the human vertebral bone.

FIG. 11 illustrates a human vertebral bone, which was used as an imaging target object when performing simulation (Monte Carlo simulation) to verify the effect of the present disclosure and a diagram simulating the structure of the human vertebral bone.

Referring to FIG. 11, the imaging target object 210 used in the present example is a human vertebral bone. A total of 45 cylinders, each made of a bone material and having a size of about 1.5 cm diameter×1 cm thickness, were formed in order to simulate the vertebral bone, and a curved section was set in the simulated vertebral bone in consideration of the flexure of the human vertebral bone.

Figure 12:
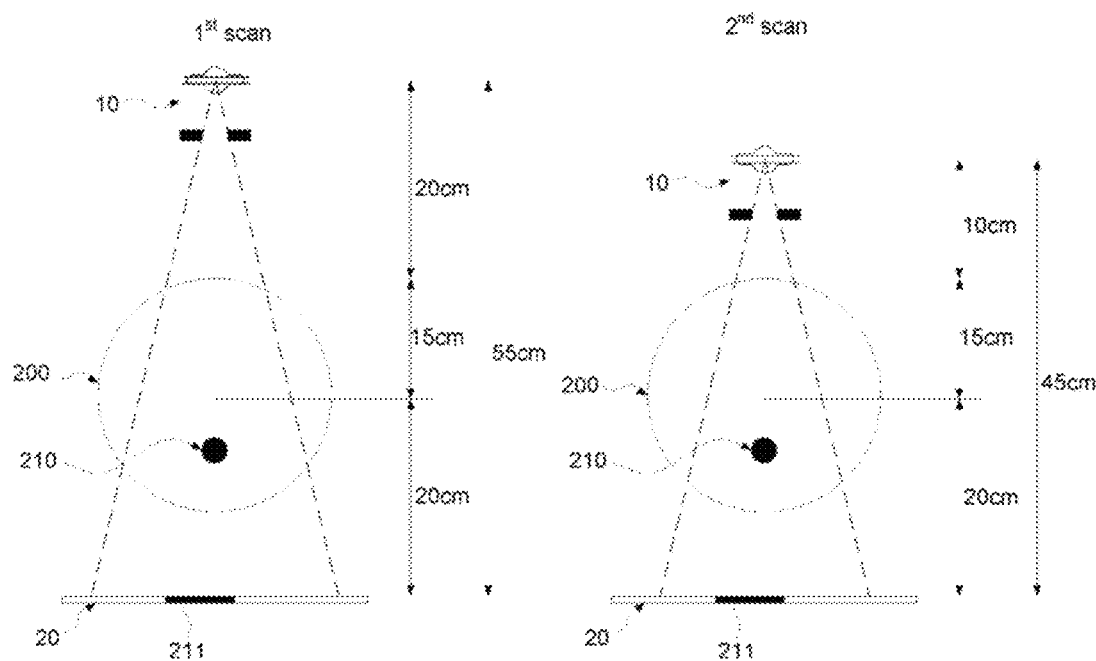
FIG. 12 schematically illustrates cross sections showing height values, which were used in the process of obtaining scan data of different heights for the human vertebral bone structure of FIG. 10.

FIG. 12 schematically illustrates cross sections showing height values, which were used in the process of obtaining scan data of different heights for the human vertebral bone structure of FIG. 10.

As illustrated in FIG. 12, during the first and second scans of the present example, the height from the x-ray detector 20 to the x-ray generator 10, the height of the x-ray generator 10, the height of the imaging target object 210, and the distance from the imaging object 210 to the x-ray generator 10 were defined.

Figure 13:
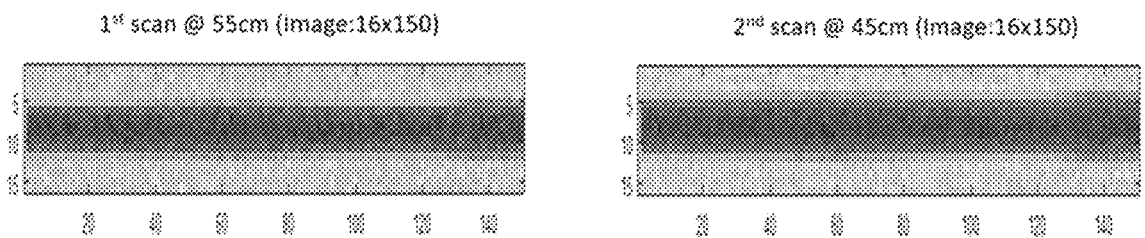
FIG. 13 illustrates data obtained through primary and secondary scans and projected on a detector.
Figure 14:
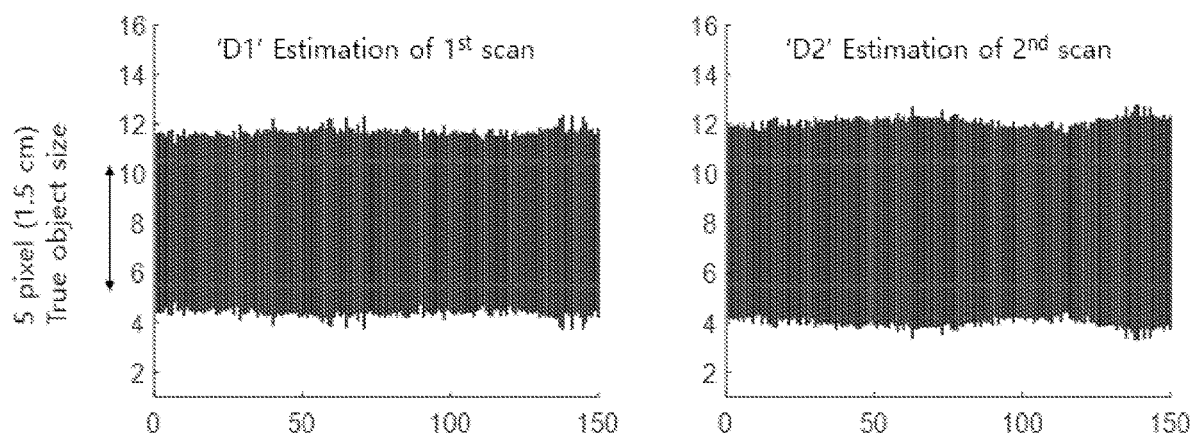
FIG. 14 illustrates imaging planes shown by extracting the size of the cross section of the vertebral bone projected on the detector of FIG. 13.

FIG. 13 illustrates data obtained through primary and secondary scans and projected on a detector, and FIG. 14 illustrates imaging planes shown by extracting the size of the cross section of the vertebral bone projected on the detector of FIG. 13.

Referring to FIG. 13, the figure illustrates imaging planes in respective graphs, in which the imaging planes were obtained by projecting the imaging target object 210 defined in FIG. 11 on the x-ray detector 20 when scans were performed twice.

Referring to FIG. 14, the figure illustrates how a vertebral bone model having a diameter of 1.5 cm and projected on the x-ray detector 20 during each scan is projected to a certain size, that is, $D_1$ or $D_2$ calculated through the method proposed in the present disclosure. Here, the red guidelines represent the actual vertebral bone size.

Figure 15:
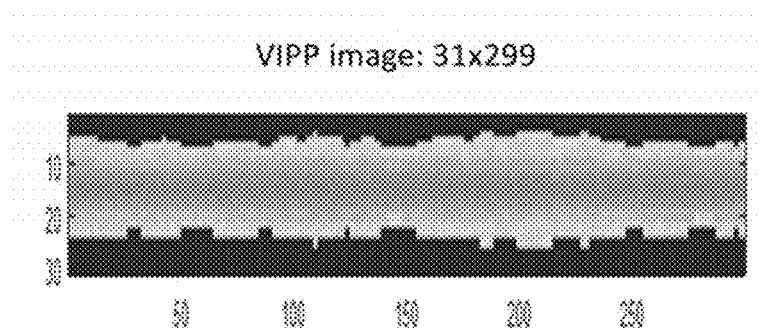
FIG. 15 illustrates projection data having a doubled resolution obtained by combining the primary scan data and the secondary scan data of FIG. 13 by applying a VIPP method.
Figure 16:
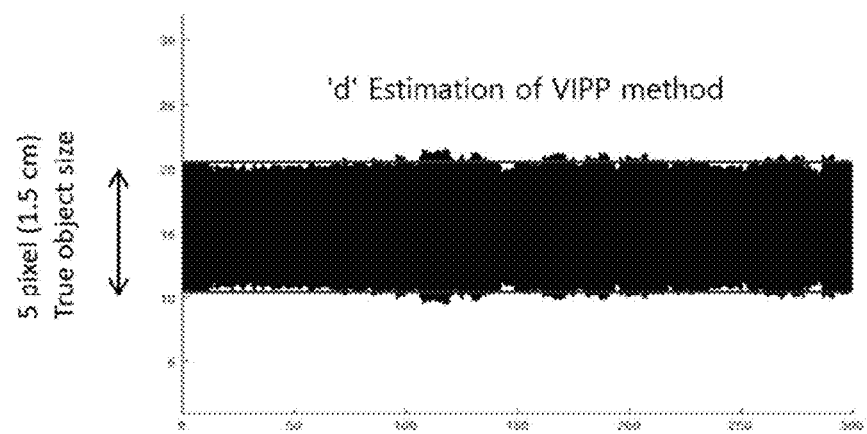
FIG. 16 illustrates an imaging plane in which only the size "d" of the cross section of the vertebral bone is extracted from the projection data acquired in FIG. 15.

FIG. 15 illustrates projection data having a doubled resolution obtained by combining the primary scan data and the secondary scan data of FIG. 13 by applying a VIPP method, and FIG. 16 illustrates an imaging plane in which only the size "d" of the cross section of the vertebral bone is extracted from the projection data acquired in FIG. 15.

Referring to FIGS. 15 and 16, the figures illustrate plane images close to an actual size in which the plane images were obtained by operating projected images or data corresponding to the size of the actual vertebral bone model by applying a Variable Imaging Plane Projection (VIPP) proposed in the present disclosure based on imaging planes collected at two different heights of the x-ray generator 10.

That is, as illustrated in FIG. 15, when the two images obtained in FIG. 13 are combined by applying the VIPP method, it is possible to obtain an image having a doubled resolution. As illustrated in FIG. 16, the size d of the actual imaging target object 210 estimated through the method proposed in the present disclosure can be calculated and displayed.

Meanwhile, Table 1 below quantifies errors occurring in each scan and quantitatively summarizes values close to the actual sizes when using the VIPP method.

TABLE 1

| Scan | 1st scan (55 cm) | 2nd scan (45 cm) | VIPP method |
|---|---|---|---|
| Image size | 16 × 150 | 16 × 150 | 31 × 299 |
| Pixel Resolution (mm/pixel) | 3 | 3 | 1.5 |
| Averaged Measured 'D' (mm) | 22.03 | 24.48 | 14.91 |
| Stand. deviation 'D' (mm) | 1.16 | 1.27 | 1.16 |
| Mean square Error (%) | 46.9 | 63.2 | 0.6 |

As represented in Table 1, it can be seen that in each scan, a size magnified to be larger than 15 mm, which is the size of the actual imaging target object 210, is projected on the detector 20. On the other hand, when using the VIPP method proposed in the present disclosure, it is proven that it is possible to obtain results very similar to actual sizes.

In addition, when applying the method of increasing the resolution described above by shifting two sets of scan data by a half pixel, it is possible to obtain an image having a resolution of 31×299 by combining two original images of 16×150. That is, a resolution of 1.5×1.5 mm can be secured using the sensors of 3×3 mm.

As described above, when an x-ray imaging method using a variable imaging plane projection of the present disclosure and an x-ray imaging device applying the x-ray imaging method are utilized, it is possible to obtain more accurate information, which is considered to be important in the corresponding x-ray imaging device during imaging using a fan-beam or cone-beam x-ray.

Meanwhile, the present disclosure is characterized in that it requires at least two scans at two different heights. Therefore, when scanning is performed while changing the energy of an x-ray during each scan, it can be effectively used for an x-ray imaging device using a dual-energy x-ray, i.e. an airport-specific baggage search stage, or for an x-ray image for bone density diagnosis.

While the present disclosure has been described above with reference to embodiments thereof, it is obvious that the present disclosure is not limited to the disclosed embodiments, that many modifications and changes can be made without departing from the scope of the present disclosure disclosed and illustrated in the claims, specification, and drawings, and that the modifications and changes belong to the scope of the present disclosure.

What is claimed is:

1. An x-ray imaging method using an x-ray imaging device having an x-ray generator and an x-ray detector which are disposed such that an imaging object is interposed therebetween, the x-ray imaging method comprising:
   obtaining at least two sets of scan data for different heights by varying a height of the x-ray generator from the x-ray detector; and
   applying a variable imaging plane projection using the at least two sets of obtained scan data to image an imaging target object in the imaging object at an actual position and size.

2. The x-ray imaging method of claim 1, wherein a size d of an imaging target object according to a height x from the imaging plane to the imaging target object is calculated by applying the variable imaging plane projection and using an equation eq1 obtained through preorder scan data and an equation eq2 obtained through postorder scan data, wherein $$\tan\theta_1 = \frac{D_1}{H_1} = \frac{d}{H_1 - x} \quad \text{eq1}$$

$$\tan\theta_2 = \frac{D_2}{H_2} = \frac{d}{H_2 - x} \quad \text{eq2}$$

where, $H_1$ and $H_2$ are heights of the x-ray generator during a preorder scan $S_1$ and a postorder scan $S_2$, $D_1$ and $D_2$ are projected sizes of the imaging object projected on the x-ray detector, $\theta_1$ and $\theta_2$ are respective projection angles at which an x-ray is projected on the imaging target object in the imaging object during the preorder scan $S_1$ and the postorder scan $S_2$, x is a height from the imaging plane to the imaging target object, and d is an actual size of the imaging target object.

3. The x-ray imaging method of claim 1, wherein the variable imaging plane projection sets variable heights of the imaging target object consecutively determined along a scan direction to x-ray projection points at respective positions at arbitrary moments, and causes the imaging target object to be projected at a calculated actual size by varying the imaging plane with respect to each of the heights at the arbitrary moments.

4. The x-ray imaging method of claim 1, wherein the x-ray generator uses a fan beam, and the x-ray detector is configured in a one-dimensional-array (1D array) type.

5. The x-ray imaging method of claim 4, wherein during the postorder scan, the scan is performed after the x-ray generator is shifted horizontally with a difference of a half pixel of the x-ray detector in comparison with the preorder scan.

6. The x-ray imaging method of claim 4, wherein, during the postorder scan, the scan is performed after the x-ray detector is shifted horizontally with a difference of a half pixel in comparison with the preorder scan.

7. The x-ray imaging method of claim 1, wherein the x-ray generator uses a cone beam, and the x-ray detector is configured in a two-dimensional-array (2D array) type.

8. The x-ray imaging method of claim 7, wherein, during the postorder scan, the scan is performed after the x-ray generator is shifted in each of vertical and horizontal directions with a difference of a half pixel of the x-ray detector in comparison with the preorder scan.

9. The x-ray imaging method of claim 7, wherein, during the postorder scan, the scan is performed after the x-ray detector is shifted in each of vertical and horizontal directions with a difference of a half pixel of the x-ray detector in comparison with the preorder scan.

10. The x-ray imaging method of claim 1, wherein scan is performed twice while varying the height of the x-ray generator, and a dual energy imaging method is applied while changing an energy of an x-ray during each scan.

11. An x-ray imaging device comprising:
   an x-ray generator configured to generate an x-ray;
   an x-ray detector disposed such that an imaging object is interposed between the x-ray generator and the x-ray detector, and configured to detect the x-ray transmitted through the imaging object;
   a first position-varying unit configured to vary a height of the x-ray generator from the imaging object; and
   an arithmetic controller configured to obtain at least two sets of scan data for different heights while varying the height of the x-ray generator from the x-ray detector through the first position-varying unit, and to image the imaging object at an actual position and size by applying a variable imaging plane projection using the at least two sets of obtained scan data.

12. The x-ray imaging device of claim 11, wherein the arithmetic controller is configured to calculate a size d of an imaging target object according to a height x from the imaging plane to the imaging target object by applying the variable imaging plane projection using an equation eq1 obtained through preorder scan data, and an equation eq2 obtained through postorder scan data, wherein $$\tan\theta_1 = \frac{D_1}{H_1} = \frac{d}{H_1 - x} \qquad \text{eq1}$$

$$\tan\theta_2 = \frac{D_2}{H_2} = \frac{d}{H_2 - x} \qquad \text{eq2}$$

where, $H_1$ and $H_2$ are heights of the x-ray generator during a preorder scan $S_1$ and a postorder scan $S_2$, $D_1$ and $D_2$ are projected sizes of the imaging object projected on the x-ray detector during the preorder scan $S_1$ and the postorder scan $S_2$, $\theta_1$ and $\theta_2$ are respective projection angles at which an x-ray is projected on the imaging target object during the preorder scan $S_1$ and the postorder scan $S_2$, x is a height from the imaging plane to the imaging target object, and d is an actual size of the imaging target object.

13. The x-ray imaging device of claim 11, wherein the arithmetic controller is configured to set variable heights of the imaging target object consecutively determined along a scan direction to x-ray projection points at respective positions at arbitrary moments by applying the variable imaging plane projection, and to cause the imaging target object to be projected in a calculated actual size by varying the imaging plane with respect to each of the heights at the arbitrary moments.

14. The x-ray imaging device of claim 11, wherein the x-ray generator is configured in a fan-beam type, and the x-ray detector is configured in a one-dimensional-array (1D array) type.

15. The x-ray imaging device of claim 14, wherein the first position-varying unit is configured to cause, during the postorder scan, the scan to be performed after the x-ray generator is shifted horizontally with a difference of a half pixel of the x-ray detector in comparison with the preorder scan.

16. The x-ray imaging device of claim 14, further comprising:
a second position-varying unit configured to vary a position of the x-ray detector,
wherein the second position-varying unit is configured to cause, during the postorder scan, the scan to be performed after the x-ray detector is shifted horizontally with a difference of a half pixel of the x-ray detector in comparison with the preorder scan.

17. The x-ray imaging device of claim 11, wherein the x-ray generator is configured in a cone-beam type, and the x-ray detector is configured in a two-dimensional-array (2D array) type.

18. The x-ray imaging device of claim 17, wherein the first position-varying unit is configured to cause, during the postorder scan, the scan to be performed after the x-ray generator is shifted in each of vertical and horizontal directions with a difference of a half pixel of the x-ray detector in comparison with the preorder scan.

19. The x-ray imaging device of claim 17, further comprising:
a second position-varying unit configured to vary a position of the x-ray detector,
wherein the second position-varying unit is configured to shift, during the postorder scan, the x-ray detector in each of vertical and horizontal directions with a difference of a half pixel of the x-ray detector in comparison with the preorder scan.

20. The x-ray imaging device of claim 11, wherein the x-ray detector is configured in a flat plate shape or an arc shape.

21. The x-ray imaging device of claim 20, wherein the x-ray detector is configured in an arc shape, and
an x-ray focal point of the x-ray generator is located at a center of the arc of the x-ray detector.

22. The x-ray imaging device of claim 11, wherein the x-ray generator is configured to vary x-ray energy during each scan when performing the scan twice while varying the height.

* * * * *